United States Patent [19]

Kaplan et al.

[11] 4,116,196

[45] Sep. 26, 1978

[54] ADDITIVE ADAPTER

[75] Inventors: Sheldon Kaplan, Potomac, Md.; Edward M. Curley, Washington, D.C.; Gerlof Homan, Olivette, Mo.

[73] Assignee: Survival Technology, Inc., Bethesda, Md.

[21] Appl. No.: 778,727

[22] Filed: Mar. 17, 1977

[51] Int. Cl.$^2$ ............................................. A61J 1/00
[52] U.S. Cl. .............................. 128/272.3; 128/218 R
[58] Field of Search .......... 128/218 R, 218 N, 218 D, 128/218 DA, 218 M, 220, 221, 215, 272.1, 272.3; 141/2, 27, 382–386

[56] References Cited

U.S. PATENT DOCUMENTS

| 2,660,168 | 11/1953 | Pontius | 128/218 D |
| 3,392,726 | 7/1968 | Pochyla et al. | 128/272.1 |
| 3,826,260 | 7/1974 | Killinger | 128/218 NV |
| 3,938,518 | 2/1976 | Tischlinger | 128/218 NV |

FOREIGN PATENT DOCUMENTS 2,442,856  11/1975  Fed. Rep. of Germany ........ 128/272.3

Primary Examiner—John D. Yasko
Attorney, Agent, or Firm—Witherspoon, Lane & Hargest

[57] ABSTRACT

An additive adapter for use in conjunction with an injector wherein the injector includes a cylindrical body having a rearward open end and a forward end necked inwardly to form an annular lip. The forward end having a central opening of reduced diameter which is closed off by a sealing diaphragm. A plunger is sealingly and slidably fitted in the rearward portion of the body to form a medicament chamber between the sealing means and the plunger. A needle hub is affixed to the annular lip and carries a needle which is in fluid communication with the medicament chamber upon the opening of the sealing diaphragm. The additive adapter comprises a main body portion including a cylindrical skirt portion extending from the rearward end of the cylindrical sleeve. The skirt is sized to snugly engage and fit over the forward portion of the injector's cylindrical body. A cylindrical shield having a diameter larger than the cylindrical sleeve extends from the forward end thereof. A cap fits on and closes off the forward open end of the shield and a retaining assembly extends inwardly from the main body portion to engage the annular lip of the necked end of the injector body to retain the adapter in assembled condition on the aforesaid body.

12 Claims, 5 Drawing Figures

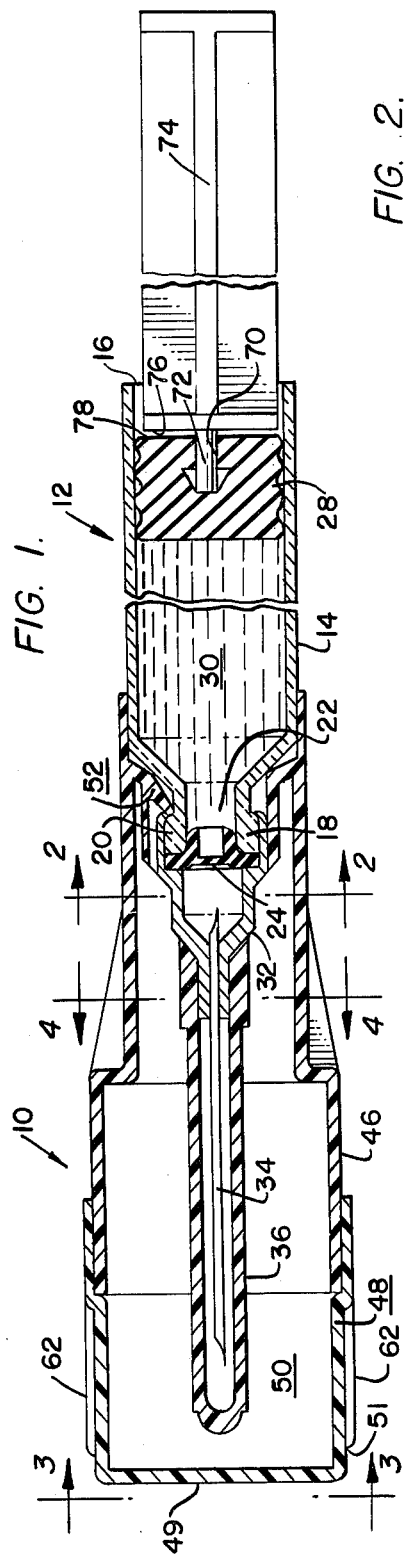
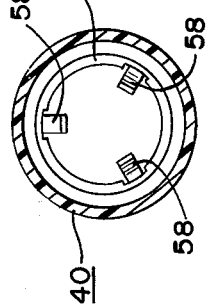
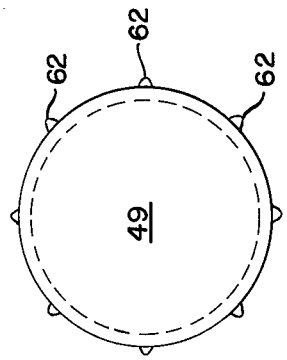
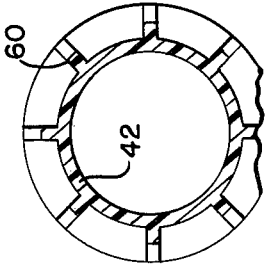
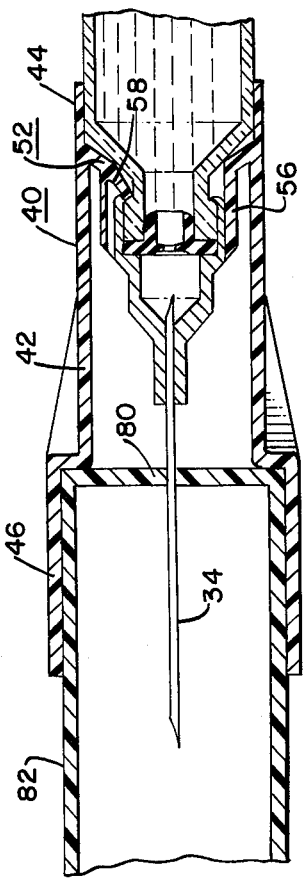

ADDITIVE ADAPTER

SUMMARY OF THE INVENTION

This invention relates to injection of medicaments and more particularly to an additive adapter for use in conjunction with an injector to make it suitable for uses other than the injecting of medicaments into a patient's body.

The ability to take an injector adapted for the injection of a medicament into a patient and to convert it to an injector adapted for injection uses other than into a patient is a very important economic benefit in the medical field. In other words, an injector unit normally filled with a medicament to be directly injected into a patient may alternatively be filled with a medicament of perhaps a concentrated nature particularly useful in I.V. units wherein a concentrated medicament is introduced into a bag feeding a patient through conventional I.V. administration apparatus. At the same time there must be assurance that the conventional injector when filled with a concentrated medicament will not be directly introduced into a patient.

In view of the foregoing it is an object of this invention to provide means whereby an injector normally used to inject medicament directly into a patient may be converted to an injector suitable only for other types of injection procedures.

It is another object of this invention to provide an adapter fitting over the needle of a conventional injector used to directly introduce medicament into a patient to adapt the unit to use as an additive injector.

It is yet another object of this invention to provide an adapter as set forth above and further wherein such adapter is designed to prevent use of the unit as an injector for introducing medicament directly into a patient.

It is a still further object of this invention to provide an injector suitable for use with an additive adapter wherein there can be no withdrawal or backward movement of the plunger as would be experienced in an aspirating or filling procedure.

The above and additional objects and advantages will become more apparent when taken in conjunction with the following detailed description of the invention and the various figures of the drawing.

IN THE DRAWINGS

FIG. 1 is a cross section view of the additive adapter of this invention installed on a conventional prefilled injector, FIG. 2 is a sectional view taken along line 2—2 of FIG. 1 showing the details of the adapter particularly the locking means, FIG. 3 is an elevational view showing the longitudinal ribs on the surface of the adapter cap, FIG. 4 is a sectional view taken along line 4—4 illustrating the longitudinal ribs on the adapter body, and FIG. 5 is a sectional view with the cap and needle shield removed and the needle of the I.V. being inserted into the open end of the adapter body.

DETAILED DESCRIPTION

As shown in the various figures of the drawing, the additive adapter 10 is used in conjunction with an injector 12 having a cylindrical body 14 with a rearward open end 16 and a forward end 18 necked inwardly to form an annular lip 20. A central opening 22 of reduced diameter is formed in the forward end of the body 14 and is closed off by means of flexible diaphragm 24 fitting on the forward face of the annular lip 20. A plunger 28 is sealingly and slidably fitted in the rearward portion of the cylindrical body 14 to form a medicament chamber 30 between the diaphragm seal 24 and the plunger 28. A needle hub 32 is affixed to annular lip 20 and mounts an injector needle 34. A needle cover 36 may be provided to maintain sterility of the needle 34. Upon the opening of the diaphragm 24 the needle 34 is in fluid communication with the medicament chamber 30.

The additive adapter 10 comprises a main body portion 40 which includes a cylindrical sleeve 42 open at its forward and rearward ends and a circular skirt portion 44 extending from the rearward end of the cylindrical sleeve 42. The skirt 44 is sized to snugly engage and fit over the forward portion of the injector's cylindrical body 14. A cylindrical shield 46 having a diameter larger than the sleeve 42 extends from the forward end thereof. A cap 48 fits over and closes off the forward open end of the shield 46 to form a closed chamber 50 in which the needle 34 is positioned. A retaining assembly 52 extends inwardly from the main body portion 40 to engage the annular lip 20 of the necked end of the injector body 14 to retain the additive adapter 10 in assembled condition on the aforesaid main body 40.

More particularly, the retaining assembly 52 comprises a cylindrical positioning member 56 extending inwardly from the main body portion 40 and fitting over the annular lip 20 of the injector body 14. Three flexible retaining fingers 58 are formed from portions of the cylindrical positioning member 56 and are equidistantly disposed thereon. The retaining fingers 58 engage the back side of the annular lip 20 to lock the adapter onto the injector 12.

In order to strengthen the adapter 10 and to assist in holding the unit, the sleeve 42 is provided with a plurality of axially extending ribs 60, see FIG 4. In addition, the cap 48 is made with a plurality of longitudinally extending ridges 62 which commence just aft of the cap top 49 and run for a distance of less than the full length of the cap side wall 51.

The construction of the additive adapter 10 is such with regard to materials and tolerances that it may be used to provide a sterile chamber for the injector needle 34. If a cover is provided for the needle 34 it could well be that the adapter would not need to form a sterile chamber therewithin. Further, the cap 48 may be affixed to the shield 46 by glue or otherwise so that if the cap is loose it will be apparent that the unit has been opened previously, thus alerting the user that another unit should be employed.

As mentioned earlier, it is intended that the adapter 10 be used with what might be termed a conventional injector so that such injector could be filled with a type of medicament used in I.V. units. This would mean that no different equipment would be required whether the injector is to be used for conventional injection or in I.V. units. Such a saving is quite attractive to the industry. Even so, there are slight modifications that could be made to the conventional injector to enhance its usefulness in I.V. work. When the present additive adapter is used in conjunction with an injector there is no intention of using any type of aspiration procedure, thus it is not necessary that the plunger rod be firmly connected to the plunger.

Referring to FIG. 1, plunger 28 is provided with a hole 70 in its rearward portion, which hole receives a rod portion 72 of the plunger 74. It should be noted that the length of the rod portion 72 is greater than the depth of the hole 70 so that the forward face 76 of the plunger rod 74 is spaced from the rearward face 78 of the plunger 28. With this arrangement retraction of the plunger rod 74 will result in withdrawal of same from the plunger 28 while forward movement of the plunger rod 74 will cause the rod portion 72 to slightly distort the plunger 28 and all the forward face 76 of the plunger rod 74 to bear against the rearward face 78 of the plunger 28 to provide even load distribution on the plunger.

The injector unit with the additive adapter affixed thereto is shipped or stored in the condition illustrated in FIG. 1 except for the plunger rod 74 which is not always assembled at such time. When it is desired to use the device, a plunger rod 74 is operatively connected to the plunger 28, if not shipped in such condition, and the cap 48 is removed. Next the needle cover 36 is removed and the device is ready for use. As illustrated in FIG. 5, the needle 34 is inserted into the end 80 of a medicament bag nipple 82. It should be noted that the nipple 82 fits within the cylindrical shield 46 of the adapter 10.

We claim:

1. An additive adapter for use in conjunction with an injector wherein the injector includes a cylindrical body having a rearward open end and a forward end necked inwardly to form an annular lip, said forward end having a central opening of reduced diameter, sealing means closing off the central opening, a plunger sealingly and slidably fitted in the rearward portion of the body to form a medicament chamber between the sealing means and the plunger, a needle hub affixed to the annular lip, a needle carried by the hub whereby its inner end will be in fluid communication with the medicament chamber upon the opening of the sealing means, the additive adapter comprising:
    a main body portion, said main body portion including a cylindrical sleeve open at its forward end and rearward end and a circular skirt portion extending from the rearward end of the cylindrical sleeve, said skirt being sized to snugly engage and fit over the cylindrical portion of the injector's cylindrical body immediately rearward of the necked portion,
    a cylindrical shield extending from the forward end of the cylindrical sleeve, and
    a retaining assembly extending inwardly from the main body portion to engage the annular lip of the necked end of the injector body to retain the adapter in assembled condition on the aforesaid body.

2. The invention as set forth in claim 1 and wherein the retaining assembly includes a plurality of resilient fingers whose free ends engage the back side of the annular lip to prevent withdrawal of the adapter from the injector.

3. The invention as set forth in claim 1 and wherein the retaining assembly comprises a cylindrical positioning member fitting over the annular lip of the injector body and retaining members formed from portions of the cylindrical positioning member, said retaining members engaging the back side of the annular lip of injector to prevent removal of the adapter from the injector.

4. The invention as set forth in claim 3 and wherein the retaining members are resilient lugs whose free ends engage the back side of the annular lip of the injector.

5. The invention as set forth in claim 1 and wherein a skirt sealingly engages the injector body and the cap sealingly closing off the open end of the shield whereby the area within the adapter which houses the needle may be rendered sterile and will then remain thus.

6. The invention as set forth in claim 1 and wherein the shield is sized and shaped to accommodate the nipple on a medicament bag.

7. The invention as set forth in claim 1 and wherein the length of the shield and the length of the injector needle are so sized that the free end of the needle will not extend far enough beyond the end of the shield to allow use of the injector as a means of injecting medicament into human patients.

8. The invention as set forth in claim 1 and wherein a cap is provided to fit on and close off the forward open end of the shield.

9. An additive injector comprising a cylindrical body having a rearward open end and a forward end necked inwardly to form an annular lip, said forward end having a central opening of reduced diameter, sealing means closing off the central opening, a plunger sealingly and slidably fitted in the rearward portion of the body to form a medicament chamber between the sealing means and the plunger, a needle hub affixed to the annular lip, a needle carried by the hub whereby its inner end will be in fluid communication with the medicament chamber upon the opening of the sealing means, and an additive adapter including:
    a main body portion, said main body portion including a cylindrical sleeve open at its forward end and rearward end and a circular skirt portion extending from the rearward end of the cylindrical sleeve, said skirt being sized to snugly engage and fit over the cylindrical portion of the injector's cylindrical body immediately rearward of the necked end portion,
    a cylindrical shield having a diameter larger than the cylindrical sleeve and extending from the forward end thereof,
    a cap fitting on and closing off the forward open end of the shield, and
    a retaining assembly extending inwardly from the main body portion to engage the annular lip of the necked end of the injector body to retain the adapter in assembled condition on the aforesaid body.

10. The invention as set forth in claim 9 and wherein the additive injector is provided with a plunger rod operatively connected to the plunger in such a manner that withdrawal of the plunger by the plunger rod is not possible.

11. The invention as set forth in claim 10 and wherein the plunger is formed with an opening in its back portion, and further wherein the plunger rod is provided with a projecting rod portion extending from its generally flat forward face, said rod portion fitting into the opening in the plunger.

12. The invention as set forth in claim 11 and wherein the rod portion of the plunger is longer than the depth of the plunger opening whereby the flat forward face of the plunger rod will be spaced from the plunger when the rod portion is fully inserted in said opening.

* * * * *